(12) United States Patent
Eckman

(10) Patent No.: US 7,699,849 B2
(45) Date of Patent: *Apr. 20, 2010

(54) DISKECTOMY INSTRUMENT WITH DISPOSABLE BLADE HEAD

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 808 days.

This patent is subject to a terminal disclaimer.

(21) Appl. No.: 11/135,219

(22) Filed: May 23, 2005

(65) Prior Publication Data

US 2005/0216019 A1    Sep. 29, 2005

Related U.S. Application Data

(63) Continuation-in-part of application No. 10/731,288, filed on Dec. 9, 2003, now Pat. No. 6,939,351, which is a continuation of application No. 10/345,525, filed on Jan. 16, 2003, now Pat. No. 6,726,690.

(60) Provisional application No. 60/369,701, filed on Apr. 2, 2002, provisional application No. 60/349,742, filed on Jan. 17, 2002.

(51) Int. Cl.
*A61B 17/32* (2006.01)

(52) U.S. Cl. ........................................ 606/79

(58) Field of Classification Search ............ 606/79, 606/80, 81, 167, 170, 180, 84, 85; 83/397, 83/620; 408/124; 433/144
See application file for complete search history.

(56) References Cited

U.S. PATENT DOCUMENTS

| 2,975,504 A | * | 3/1961 | Bentham | 407/29.12 |
| 3,702,611 A | | 11/1972 | Fishbein | |
| 3,967,377 A | | 7/1976 | Wells | |
| 4,349,921 A | | 9/1982 | Kuntz | |
| 4,473,076 A | | 9/1984 | Williams et al. | |
| 4,499,898 A | | 2/1985 | Knepshield et al. | |
| 4,884,569 A | | 12/1989 | Federov et al. | |
| 5,203,865 A | | 4/1993 | Siepser | |
| 5,209,799 A | | 5/1993 | Vigil | |
| 5,224,945 A | | 7/1993 | Pannek, Jr. | |

(Continued)

OTHER PUBLICATIONS

Albee, Fred H., M.D., F.A.C.S, Bone Surgery with Machine Tools, Scientific American, Apr. 1936, 178-181.*

*Primary Examiner*—Eduardo C Robert
*Assistant Examiner*—David Comstock
(74) *Attorney, Agent, or Firm*—Panitch Schwarze Belisario & Nadel LLP

(57) ABSTRACT

A diskectomy instrument includes a blade housing assembly having a first housing portion and a second housing portion. The second portion is fixedly attached to a probe body, and the first portion is releasably connectable to the second portion. At least one blade opening is provided, and at least one blade is movably mounted at least partially within the blade housing for movement through the at least one blade opening between an extended position and a retracted position. A drive stem is movably mounted for linear movement within the probe body and is operatively connected to an actuator. The drive stem engages the at least one blade to move the blade between the extended position and the retracted position. A removal tool is provided to permit the first housing portion to be removed from the second housing portion.

8 Claims, 12 Drawing Sheets

U.S. PATENT DOCUMENTS

| | | |
|---|---|---|
| 5,242,017 A | 9/1993 | Hailey |
| 5,403,276 A | 4/1995 | Schechter et al. |
| 5,445,639 A | 8/1995 | Kuslich et al. |
| 5,620,453 A | 4/1997 | Nallakrishnan |
| 5,620,456 A | 4/1997 | Sauer et al. |
| 5,645,549 A | 7/1997 | Boyd et al. |
| 5,669,876 A | 9/1997 | Schechter et al. |
| 5,685,840 A | 11/1997 | Schechter et al. |
| 5,755,719 A * | 5/1998 | Frieze et al. .................. 606/81 |
| 5,797,939 A | 8/1998 | Yoon |
| 5,827,305 A | 10/1998 | Gordon |
| 5,833,692 A | 11/1998 | Cesarini et al. |
| 5,853,054 A | 12/1998 | McGarian et al. |
| 5,885,292 A | 3/1999 | Moskovitz et al. |
| 5,908,432 A | 6/1999 | Pan |
| 5,928,239 A | 7/1999 | Mirza |
| 5,935,144 A | 8/1999 | Estabrook |
| 6,022,362 A | 2/2000 | Lee et al. |
| 6,171,312 B1 | 1/2001 | Beaty |
| 6,383,188 B2 | 5/2002 | Kuslich et al. |
| 6,783,533 B2 | 8/2004 | Green |
| 6,976,968 B2 * | 12/2005 | Ritchart et al. ............... 600/567 |
| 2002/0138078 A1 | 9/2002 | Chappuis |

\* cited by examiner

DISKECTOMY INSTRUMENT WITH DISPOSABLE BLADE HEAD

CROSS-REFERENCES TO RELATED APPLICATIONS

This application is a continuation-in-part of U.S. patent application Ser. No. 10/731,288 filed Dec. 9, 2003, entitled "Diskectomy Instrument and Method" now issued as U.S. Pat. No. 6,939,351, which is a continuation of U.S. patent application Ser. No. 10/345,525, filed Jan. 16, 2003, entitled "Diskectomy Instrument and Method", now issued as U.S. Pat. No. 6,726,690, which claimed the benefit of U.S. Provisional Application No. 60/369,701 filed Apr. 2, 2002 entitled "Diskectomy Instrument and Method" and U.S. Provisional Application No. 60/349,742 filed Jan. 17, 2002 entitled "Diskectomy Instrument and Method". The entire contents of each of the above-identified applications are incorporated by reference herein.

BACKGROUND OF THE INVENTION

The present invention relates to an apparatus for performing diskectomy and more particularly to an instrument for performing partial diskectomies having a disposable blade head.

Referring to prior art FIGS. 9 and 10, the spine 120, also known as the vertebral column or the spinal column, is a flexible column of vertebrae 100 (special types of bones) held together by muscles, ligaments and tendons. The spine 120 extends from the cranium (not shown) to the coccyx 126, encasing a spinal cord 128 and forming the supporting axis of the body (not shown). The spinal cord 128 is a thick bundle of nerve tissue (nerves) that branch off to various areas of the body for the purposes of motor control, sensation, and the like. The spine 120 includes seven cervical vertebrae (not shown), twelve thoracic vertebrae (not shown), five lumbar vertebrae, $L^I$-$L^V$, five sacral vertebrae, $S^I$-$S^V$, and three coccyx vertebrae 126. The sacral and coccyx vertebrae are each fused, thereby functioning as a single unit. FIG. 10 shows the lumbar region 122, the sacral region 124 and the coccyx 126 of the spine 120 and that the vertebrae 100 are stacked one upon another. The top portion 100a and bottom portion 100b of each vertebrae 100 is slightly concave. The opposing concave vertebral surfaces form the intervertebral space 121 in which an intervertebral disk (not shown) resides. Each of the intervertebral disks has a soft core referred to as a nucleus pulposus or nucleus (not shown).

In FIG. 9, directional arrow 101a is pointing in the posterior direction and directional arrow 101b is pointing in the anterior direction. FIG. 9 shows that each vertebrae 100 includes a body 106 in the innermost portion, a spinal canal 108 and a spinous process 102 at the posterior-most end of the vertebra 100. The vertebrae 100 are substantially similar in composition, but vary in size from the larger lumbar to the smallest coccyx vertebrae 126. Each vertebrae 100 further includes two transverse processes 104 located on either side and a protective plate-like structure referred to as a lamina 110. Nerves from the spinal cord 128 pass through the spinal canal 108 and foramina 111 to reach their respective destinations within the body.

The natural aging process can cause a deterioration of the intervertebral disks, and therefore, their intrinsic support strength and stability is diminished. Sudden movements may cause a disk to rupture or herniate. A herniation of the disk is primarily a problem when the nucleus pulposus protrudes or ruptures into the spinal canal 108 placing pressure on nerves which in turn causes spasms, tingling, numbness, and/or pain in one or more parts of the body, depending on the nerves involved. Further deterioration of the disk can cause the damaged disk to lose height and as bone spurs develop on the vertebrae 100, result in a narrowing of the spinal canal 108 and foramen 111, and thereby causes pressure on the nerves emanating from the spinal cord 128.

Presently, there are several techniques, in addition to non-surgical treatments, for relieving the symptoms related to intervertebral disk deterioration. Surgical options include chemonucleolysis, laminectomy, diskectomy, microdiskectomy, and spinal fusion.

Chemonucleolysis is the injection of an enzyme, such as chymopapain, into the disk to dissolve the protruding nucleus pulposus. The enzyme is a protein-digesting enzyme and is used to dissolve the disk material. Since the enzyme is essentially a tissue-dissolving agent, it is indiscriminate in the protein-based matter it dissolves. Should the enzyme be injected into the wrong place, or if there is a breach in the disk capsule that would allow the solution to enter the spinal canal or to contact nerve tissue or the like, the resultant damage to nerve tissue could not be reversed. Even worse, about half of the patients who receive chemonucleolysis treatments experience increased back pain and muscle spasms immediately after the injection and more than half have incapacitating back pain for durations up to three months after such treatments.

A laminectomy is performed to decompress the spinal canal 108 by open surgical techniques under general anesthesia. In this procedure, the lamina 110, (the bone that curves around and covers the spinal canal 108 as shown in FIG. 9), and any disk tissue causing pressure on a nerve or the spinal canal 108, are partially removed. This technique is highly invasive and traumatic to the body, and therefore requires an extended recovery time of about five weeks and a hospital stay of a few days. In addition to the trauma inflicted on the body from even a successful surgery, there are increased risks of future problems due to the removed portion of the lamina 110 which is no longer in place to support and protect the spinal canal 108 at the area where the surgery took place. Further, the vertebrae 100 may shift due to the lack of support in the structure. Thus, simply removing the disk and parts of the vertebral bone is a short-term, pain-relieving corrective action but not a long-term solution.

Diskectomy is a form of spinal surgery wherein part or all of an intervertebral disk is excised typically through open surgical techniques. Recently, less invasive techniques referred to as percutaneous diskectomy or microdiskectomy have been developed to reduce the surgical trauma to the patient. In microdiskectomy, a much smaller incision is made than in normal open surgeries. A small retractor, working channel or tube is inserted through the posterior muscles (not shown) to allow access to the damaged or herniated disk. Surgeons utilize special surgical instruments modified to work in such small openings such as curettes, osteotomes, reamers, probes, retractors, forceps, and the like to cut and remove part of the disk while monitoring their technique using a microscope, fluoroscope (real-time X-ray monitoring), and/or an endoscope (a miniature TV camera with associated viewing monitor). While this technique is much less invasive than conventional open surgeries, due to their design the instruments presently available tend to extend the length of time of the surgery and may cause possible damage to areas other than the herniated disk. For example, the curette is a spoon-shaped instrument with a sharp edge that is used mainly to scrape the nucleus pulposus matter (not shown) from the end plates of the vertebral bones. Since the blade is unprotected, there is potential for damage to the surrounding nerves and ligaments during insertion and during use. Further, due to the varying concavity of the vertebral space (or the concavity of the top and bottom portions 100a, b of the vertebral bones) it is often a time consuming procedure for the surgeon to repeatedly scrape at varying angles using the curette. Another instrument that is often used is the reamer (not shown) which is intended to remove the nucleus pulposus matter more quickly than a curette. The reamer is usually a cylindrically-shaped, drill-bit-like device with a flat tip and a plurality of sharp edges along its outer sides. The reamer is continuously turned inside the vertebral disk space 121 to scrape the nucleus pulposus matter from the vertebral bones; however, reamers often cause damage to adjacent vertebrae and may cause damage to nerves, blood vessels and/or ligaments while being inserted into the intervertebral space.

The removal of a significant amount of disk material or numerous surgeries often increases the instability of the spine 120 thereby necessitating spinal fusion surgery. In a fusion procedure, a damaged disk may be completely removed. Parts of a bone from another part of the body, such as the pelvis, are harvested, and the bone parts or grafts are subsequently placed between the adjacent vertebrae 100 so that the adjacent vertebrae 100 grow together in a solid mass. In the fusion surgery, which is presently performed as an open surgical technique, the posterior lamina 110 and the centers of the vertebral bodies 106 may both be cut. The surgery often involves consequential damage to the associated posterior ligaments, muscles and joints in addition to the removal of part or all of the lamina 110. The recovery time for a normal spinal fusion surgery is significant due not only to the fact that normal movement cannot be allowed until detectable bone growth has occurred between the bone grafts and the adjacent vertebrae 100, but the associated ligaments, muscles and the location where the bone grafts were harvested must also recover. Oftentimes portions of the spine 120 must be immobilized during the recovery period causing added discomfort and inconvenience to the patient.

What is required, but not presently provided by the prior art devices and methods, is a surgical instrument for performing partial diskectomies that is minimally invasive, easy to use, safe to insert into the body during surgery, provides rapid removal of the nucleus pulposus matter, and which does not cause undesired damage to adjacent vertebrae. What is further required is a micro surgical technique that allows for fast patient recovery times and that can be used on an outpatient basis.

BRIEF SUMMARY OF THE INVENTION

Briefly stated, in a first aspect the present invention is a diskectomy instrument comprising a probe body and a blade housing assembly including a first housing portion and a second housing portion. The second housing portion is fixedly attached to the probe body, and the first housing portion is releasably connectable to the second housing portion. At least one blade opening is provided in the blade housing assembly. At least one blade is movably mounted at least partially within the blade housing for movement through the at least one blade opening between an extended position and a retracted position. A drive stem is movably mounted for linear movement within the probe body and is operatively connected to an actuator for movement between a first position and a second position. With the drive stem in the first position, the drive stem slidably engages the at least one blade to drive the at least one blade into the blade extended position. With the drive stem in the second position, the drive stem slidably engages the at least one blade to drive the at least one blade into the blade retracted position.

In a second aspect, the present invention is a removal tool in combination with a diskectomy instrument. The combination comprises a diskectomy instrument having a blade housing with a removable first portion and at least one blade at least partially contained within the blade housing. A removal tool includes a pair of opposing handles joined by a hinge, each handle having a clamping section provided with at least one protruding element sized, shaped, and positioned such that with the removal tool in a closed position, the protruding elements each engage an exterior surface of the blade housing to compress an outer wall of the blade housing and release the first portion from engagement with a remainder of the blade housing.

In yet a third aspect, the invention is a bi-directional blade in combination with a diskectomy instrument including a body and a drive stem having a blade mating portion. The bi-directional blade comprises an edge having a central plane and a plurality of cutting elements arranged along the edge, each cutting element having a sharpened cutting edge. Adjacent cutting elements are separated by blunt spacer elements.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
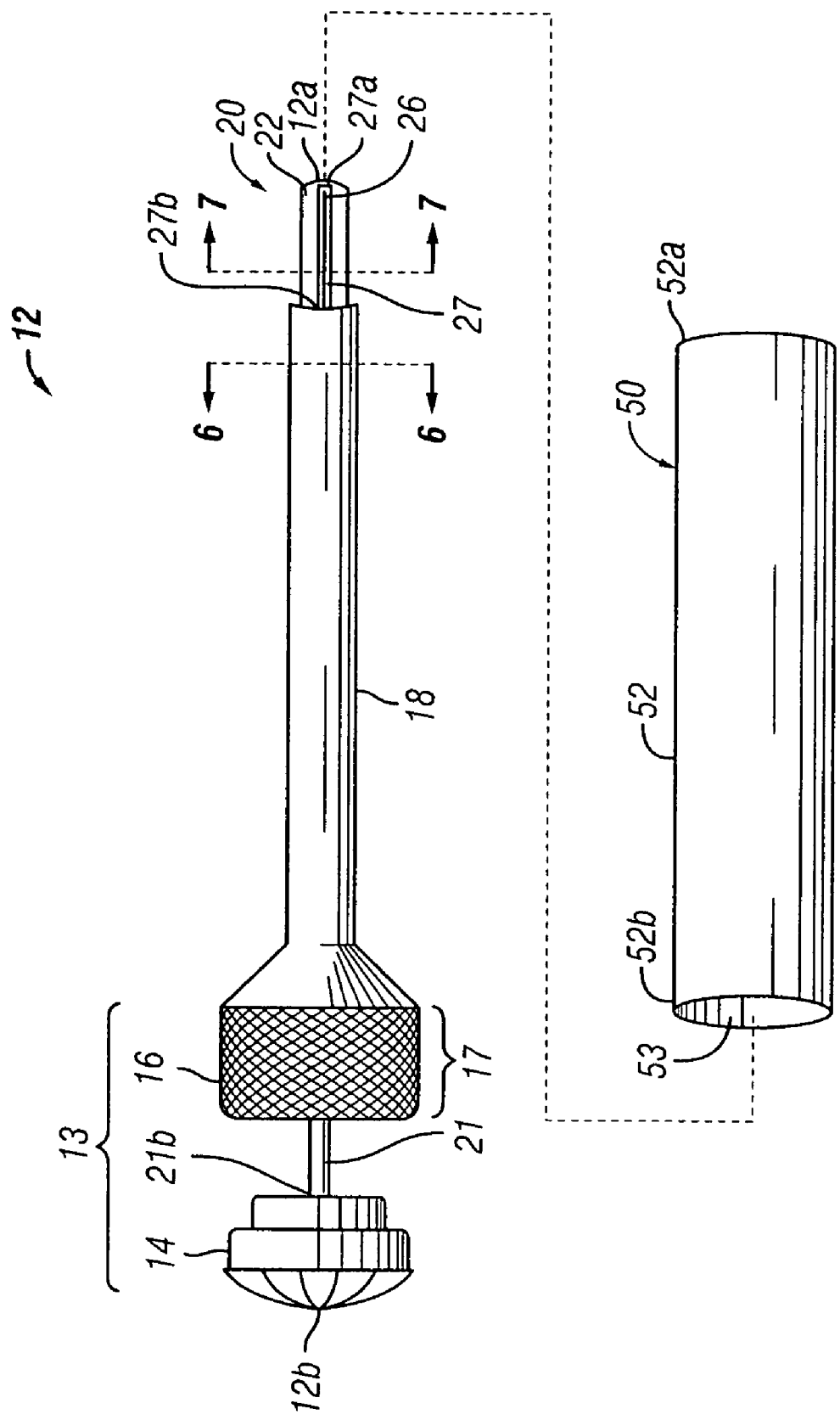
FIG. 1 is a side elevational view of a diskectomy instrument in accordance with a first preferred embodiment of the present invention.

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the diskectomy instrument and designated parts thereof. The terminology includes the words above specifically mentioned, derivatives thereof and words of similar import. Additionally, the word "a", as used in the claims and in the corresponding portions of the specification, means "at least one."

Referring to the drawings in detail, wherein like reference numerals indicate like elements throughout, there is shown in FIG. 1 a diskectomy instrument 12 in accordance with a first preferred embodiment of the present invention. The diskectomy instrument 12 includes an elongate body 18, a probe assembly 20, an actuator mechanism 13, a blade positioning knob 14 and a handle or blade rotation knob 16. The diskectomy instrument 12 has a distal end 12a and a proximal end 12b. Obviously, the probe assembly 20 can be integral or part of the elongate body 18. The portions of the diskectomy instrument 12 intended to contact internal human body matter are formed of a biologically compatible material selected such as stainless steel, titanium, nickel plated metal, any biocompatible metal or alloy, a biocompatible ceramic, a biocompatible polymeric material and the like.

The elongate body 18 is between about 5 mm and 30 mm in diameter making it ideally suited for use in outpatient minimally invasive surgery. Preferably, the diskectomy instrument 12 is used in combination with a working tube 50 of only slightly greater diameter which provides a portal to the small gap between two adjacent vertebrae 100 as will be described in greater detail hereinafter. The working tube 50 preferably has an elongate housing 52 having a distal end 52a, a proximal end 52b and an interior lumen 53 traversing through the elongate housing 52. The working tube is configured to be inserted through an incision between about 5 mm and about 100 mm in span, but is more preferably configured to be inserted through an incision of less than about 25 mm in span. Of course the working tube 50 and the diskectomy tool 12 can be configured to be inserted through incisions or openings having other dimensions and can be used in conventional open surgery without departing from the present invention.

Figure 2:
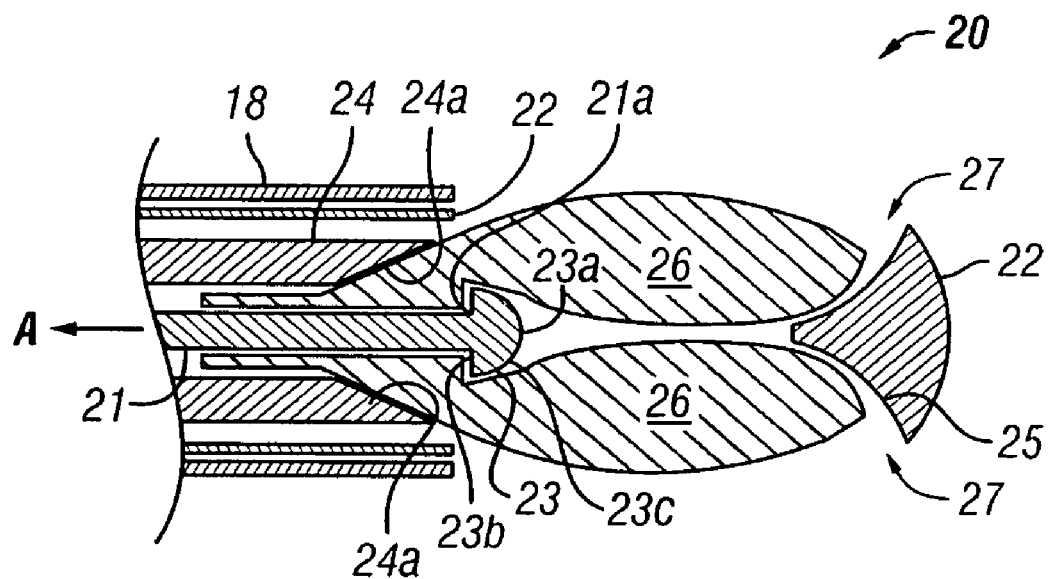
FIG. 2 is a greatly enlarged side sectional view of a portion of the diskectomy instrument of FIG. 1 in a retracted position.

FIG. 2 shows a side cutaway of the distal end 12a of the diskectomy instrument 12 providing a much more detailed view of the probe assembly 20. The probe assembly 20 includes a probe body 22, a drive stem 21, an inner sheath 24, a biasing cone 25 and at least one blade 26. The probe body 22 includes a blade opening 27 for each blade 26. The blade opening 27 has a distal end 27a and a proximal end 27b. Preferably each blade opening 27 is generally rectangularly-shaped. But, the blade openings 27 may be other shapes. The blade openings 27 are selected to be only slightly wider than the blades 26 in order to provide lateral support to the blades 26 when the blades 26 are radially extended. The close tolerance between the blade openings 27 and the blades 26 also assists in preventing foreign materials from being trapped in between the blades 26 and the blade openings 27 when the blades 26 are being retracted.

The drive stem 21 has a distal end 21a and a proximal end 21b (FIG. 1). A stem end-cap 23 is positioned on the distal end 21a of the drive stem 21 and includes a proximal end 23b and a distal end 23a, the distal end preferably being configured as a dome-shaped or rounded conically-shaped surface 23c as discussed more fully below. The proximal end 23b and the dome-shaped surface 23c of the stem end-cap 23 form a blade mating portion 23b, 23c of the drive stem 21. The drive stem 21 is slidably mounted within the probe 20 and is configured to slidably engage the blades 26 when the drive stem 21 is moved distally thereby moving the distal and proximal ends 26a, 26b of the blades 26 distally, radially away from and generally parallel to a longitudinal axis of the diskectomy instrument 12 and extending the blades 26 radially outward through the blade openings 27. The drive stem 21, or more particularly, the blade mating portion(s) 23b, 23c of the drive stem 21 is configured to cooperatively engage a stem mating portion 29 of the blades 26 when the drive stem 21 is moved proximally thereby moving the blades 26 proximally and retracting the blades 26 radially inward. Of course other more complicated mechanical arrangements may be coupled between the drive stem 21 and the blades 26 without departing from the present invention.

Figure 7:
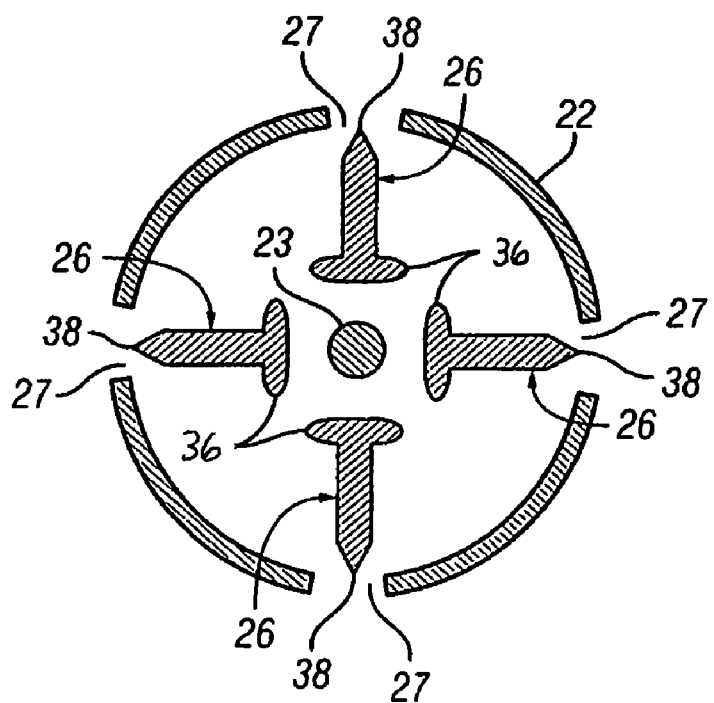
FIG. 7 is a greatly enlarged sectional view of a portion of the diskectomy instrument taken along line 7-7, FIG. 1.
Figure 8:
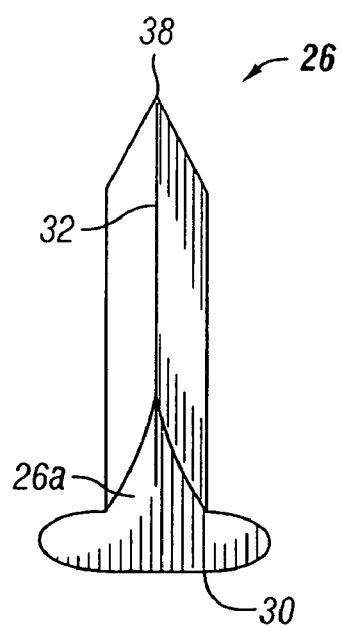
FIG. 8 is a front elevational view of the blade of FIG. 4.

Preferably, there are four blades 26 (see FIGS. 7 and 8). When configured with four or more blades 26, the diskectomy tool 12 is more stable during a cutting procedure and can more easily find the most concave portions 100a or 100b of a particular vertebra 100. But, there may be any number of blades 26 without departing from the spirit of the invention. Each of the blades 26 (FIGS. 4-5) is preferably identical and includes a distal end 26a and proximal end 26b. It is contemplated, however, that the blades 26 need not be identical to one another and that the blades 26 may also be matched in opposing pairs or may each be unique with respect to the others.

Figure 4:
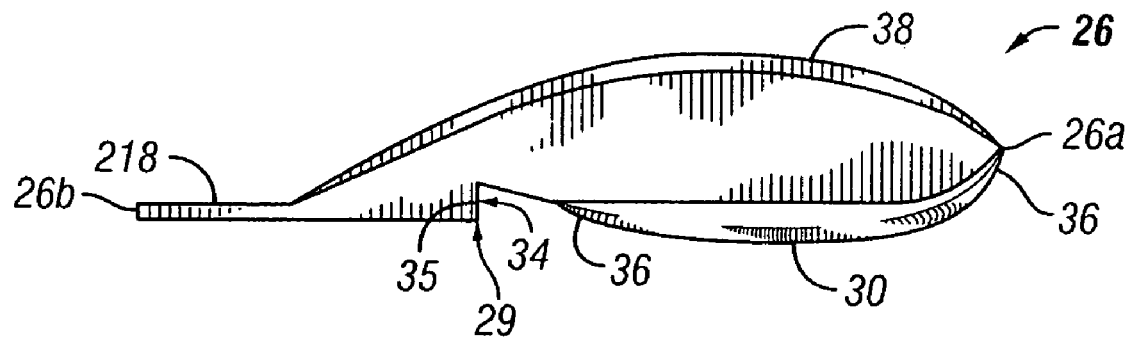
FIG. 4 is a side elevational view of a blade used in a diskectomy instrument in accordance with the present invention.
Figure 5:
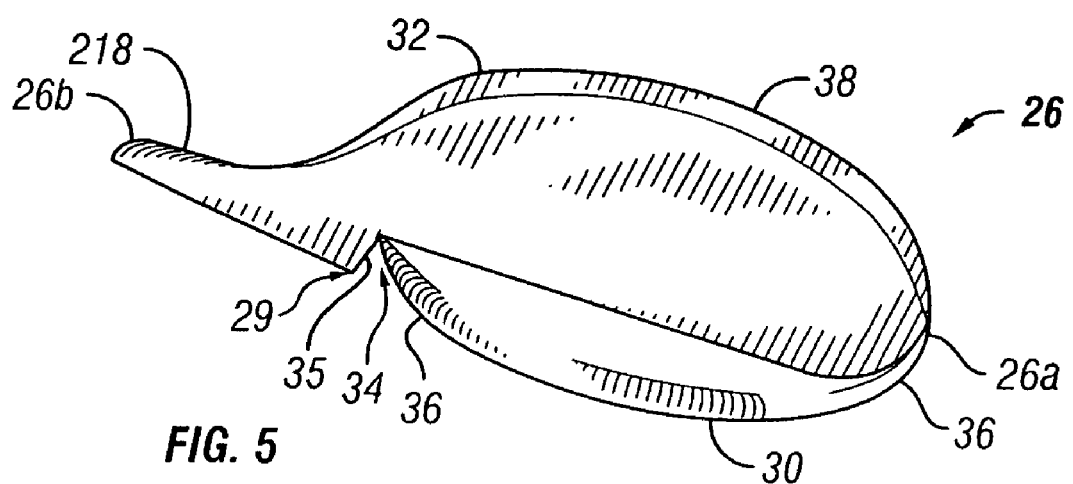
FIG. 5 is a perspective view of the blade of FIG. 4.
Figure 6:
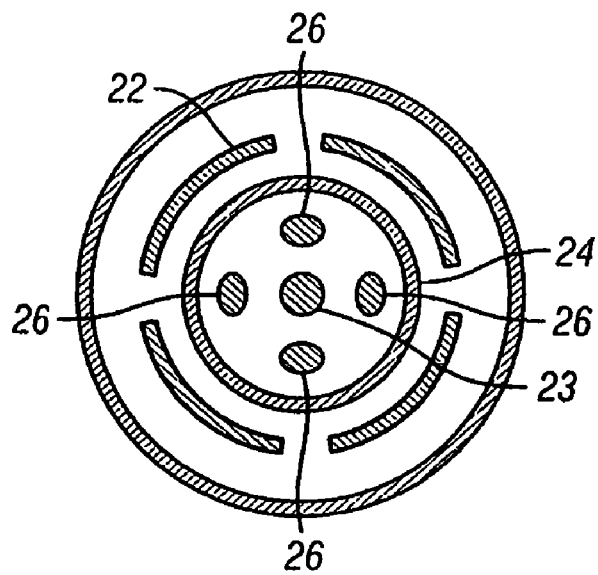
FIG. 6 is a greatly enlarged sectional view of a portion of the diskectomy instrument taken along line 6-6, FIG. 1.

The blades 26 are preferably formed of a hard, bio-compatible metal such as stainless steel, titanium, nickel, metal alloy, or the like. But, the blades 26 can be formed of other materials. It should be noted that the blades 26 are rigid. Each blade 26 preferably has an asymmetrical shape as best shown in FIGS. 4-5; however, the blades 26 may be other shapes without departing from the broad scope of the present invention. Preferably, the blades are generally convexly-shaped proximate the at least one sharp edge 32 thereby allowing the blades 26 to naturally find the most concave portions 100a or 100b of a particular vertebra 100.

The blades 26 may be reusable after suitable sterilization as is known in the art, but preferably, the blades 26 are disposable. Accordingly, the blades 26 are preferably removably and movably mounted in the probe 20 within the elongate body 18 of the diskectomy tool 12. In one embodiment, the distal end 12a of the diskectomy instrument 12 is at least partially open or the end of the probe 20 is removable to allow the blades 26 to be removed from the distal end 12a of the diskectomy tool 12. Preferably, however, the blades 26 are removed proximally through the elongate body 18 allowing the end of the probe 20 to be generally closed and bluntly rounded.

Referring to FIGS. 4-5 and 7, each blade has an inner face 30 and an outer surface 32 having at least one sharpened edge 38 extending at least partially between the distal end 26a and the proximal end 26b of the blade 26. The stem mating portion 29 of the blades 26 are configured to cooperatively engage the blade mating portion 23b, 23c of the drive stem 21. Preferably, each blade 26 includes a notch 34 having a retracting ledge 35 defining the stem mating portion 29, and each blade 26 also includes at least one extending ramp 36 extending generally perpendicularly from a sidewall of each blade 26. Preferably, each blade 26 has two or more ramps 36 to firmly guide the blade 26 radially outward. The retracting ledge 35 accommodates a portion of the proximal end 23b of the stem end-cap 23 which defines the blade mating portion 23b, 23c of the drive stem 21. The extending ramp 36 cooperates with the dome-shaped surface 23c of the end-cap 23. The end-cap 23 is attached to or integrally formed with the drive stem 21 at the most distal end 21a of the drive stem 21. The end-cap 23 is preferably hemispherically-shaped wherein the proximal end 23b is generally flat and the distal end 23a includes the spherical portion defining the dome-shaped surface 23c. While the stem end-cap 23 of the preferred embodiments is hemispherically shaped, the stem end-cap 23 may have other shapes such as an egg shape, a bullet shape, a conical shape, a pyramidal shape or the like without departing from the broad inventive concept herein. Furthermore, the stem end-cap 23 may also have other cooperative shapes and/or structures as well including for example protuberances and detents. For example, if the blade mating portion 23b, 23c of the drive stem 21 is a protuberance then the stem mating portion 29 of the blade 26 is a cooperatively shaped indentation or the like. Likewise, if the blade mating portion 23b, 23c of the drive stem 21 is an indentation then the stem mating portion 29 of the blade 26 is a cooperatively shaped protuberance. Of course, the blade mating portion 23b, 23c of the drive stem 21 and the stem mating portion 29 of the blade 26 may be other cooperative shapes suitable for engaging one another without departing from the present invention.

Preferably, each blade 26 includes a bidirectional sharp cutting edge 38 spanning both sides of the blade 26. The blades 26 may also include a plurality of sharp cutting edges 38 emanating from the same side of the at least one sharpened edge 38. Alternatively, the blades 26 include only one sharpened edge 28 facing one direction. Thus, during use when the blades 26 are rotated in the cutting direction, the sharpened edges 38 tend to cut but when the blades 26 are rotated in the opposite direction the blades 26 tend not to cut. Of course the blades 26 could be designed to cut in either direction or both directions without departing from the present invention.

The distal end 26a of the blade 26 is preferably blunted or dull to cooperatively engage the biasing cone 25 when the stem 21 pushes the blades 26 with force in the distal direction thereby causing the blades 26 to move distally and radially outward. In an alternate embodiment, the elongate body 18 further comprises a fixed abutment (not shown) configured to engage the ramp 36 when the drive stem 21 is moved distally thereby assisting in extending the blades 26 radially outward.

The probe assembly 20 is mechanically coupled by known methods to either the elongate body 18 or the interior portion of the blade rotation knob 16 such that rotation of the blade rotation knob 16 in turn rotates the probe assembly 20 thereby rotating the blades 26. The blade rotation knob 16 is preferably coupled to the blades 26 and rotating the blade rotation knob 26 causes the blades 26 to rotate in a cutting direction.

The proximal end 26b of the blades 26 is sloped such that the proximal end of surface 32 cooperatively engages an inner wedged surface 24a of the inner sheath 24. Proximal movement of the blades 26 causes a sloped portion of each outer surface 32 to engage the inner wedged surface 24a of the inner sheath 24, thereby causing the blades 26 to also retract inwardly as well as proximally. Optionally, the proximal end 27a of the blade openings 27 also engages the sloped portion of the outer surface 32, thereby assisting the inner wedged surface 24a of the inner sheath 24 in imparting inward movement on the blades 26. Such a configuration provides the surgeon or other user with a mechanical advantage when retracting the blades 26 so that foreign matter can be easily jettisoned from the blades 26 as they are retracted through the blade openings 27.

Figure 9:
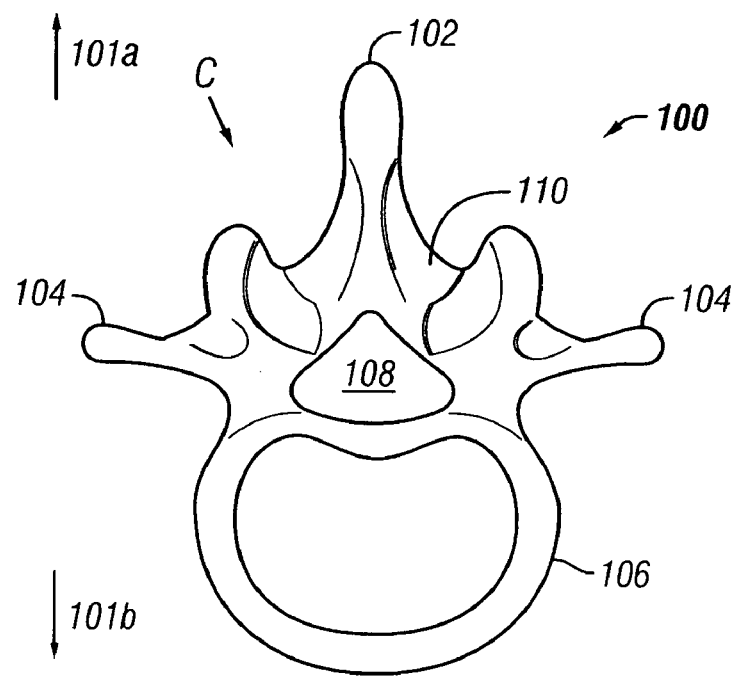
FIG. 9 is a top sectional view of a human vertebrae as is known in the art.
Figure 10:
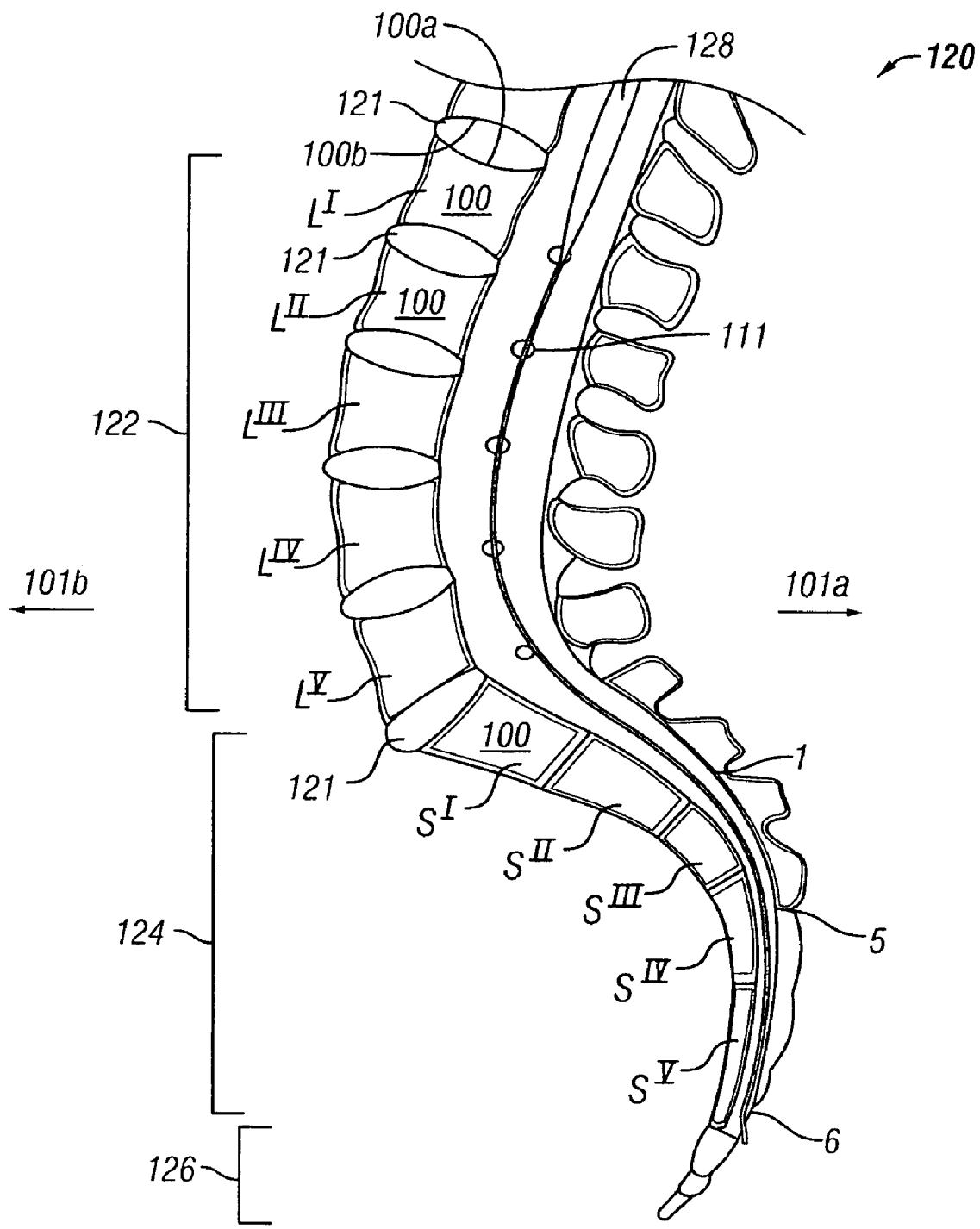
FIG. 10 is a side sectional view of the lumbar and sacral regions of a human spine as in known in the art.

In operation, the blade positioning knob 14 is moved proximally which pulls drive stem 21 in the direction of arrow A (FIG. 2) causing the proximal end 23b of the stem cap 23 to engage the retracting ledge 35, thereby biasing the blades 26 inwardly and proximally toward the inner sheath 24. The distal end 12a of the diskectomy instrument 12 is then inserted through the working tube 50 as is known in the art and into a small gap between a first vertebra and a second adjacent vertebra. Since the distal end 12a of the diskectomy instrument 12 is somewhat blunted, there is minimal risk of damaging ligaments, muscles, nerves, or the like during the insertion process. Preferably, the diskectomy instrument 12 is inserted from the posterior direction 101a at a location off-center such as in the direction of Arrow C (FIG. 9). While the diskectomy instrument 12 is described in the context of microdiskectomy surgery, uses of the instrument 12 are not limited to such surgeries. It is also possible to use the diskectomy instrument 12 in conventional open surgeries such as laminectomies, diskectomies, spinal fusions, and the like.

Figure 3:
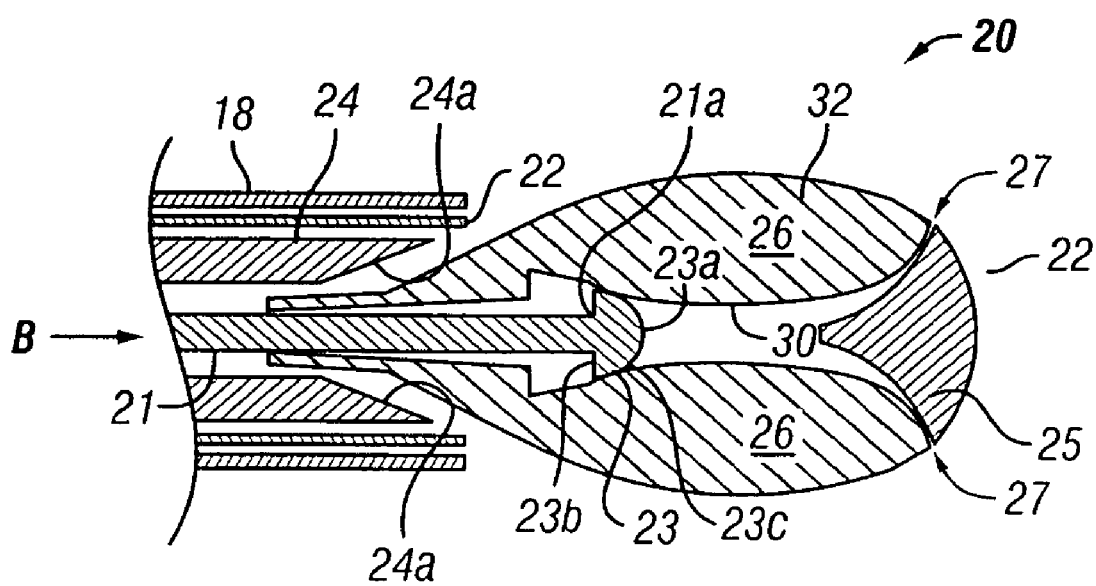
FIG. 3 is a greatly enlarged side sectional view of a portion of diskectomy instrument of FIG. 1 in an extended position.

Once the distal end 12a of the diskectomy instrument 12 is within the intervertebral disk space 121 (FIG. 9), the surgeon can press or rotate the blade positioning knob 14 driving the drive stem 21 distally. The drive stem 21 moves distally in the direction of arrow B (FIG. 3) causing the dome-shaped surface 23c of the stem cap 23 to cooperatively engage the extending ramps 36 of the blades 26 and forcing the distal end 26a of the blades 26 to engage the biasing cone 25 thereby causing the blades 26 to move outwardly such that the sharpened edge 38 extends through the blade openings 27 and beyond the outside of the probe assembly 20.

After the blades 26 have been extended, the surgeon rotates the blade rotation knob 16 in either a clockwise or counter-clockwise direction, depending on the direction of the sharpened edge 38 of the blades 26, causing the probe assembly 20 and the associated blades 26 to rotate therewith and providing a rapid debridement of the nucleus pulposus of the intervertebral disk. Unlike conventional prior art curettes and reamers, the curved and outwardly-biased blades 26 (as best shown in FIG. 5) accommodate the natural concavity of the adjacent vertebrae 100 which significantly reduces the amount of time required to enucleate the disk space 121. If desired, the blades 26 will allow abrasion of the top concave portion 100a of a vertebra and the opposing lower concave portion 100b of the adjacent vertebra to encourage bone ingrowth into devices such as artificial disks, bone grafts, non-bone fusion devices, and the like. If desired, the blades 26 can be used for the partial removal of the end plate (not shown clearly). Due to the size and smooth contour shape of the blades 26, the outer layers of annular ligament and the majority of circumferential edges of the vertebral bodies 106 are able to be preserved which is beneficial to the support of the vertebrae 100 when an interbody device such as an artificial disk or a fusion apparatus is installed after the diskectomy procedure is completed. Such a diskectomy instrument 12 is ideally suited for only removing the nucleus between two adjacent vertebrae 100 while only minimally removing parts of the surrounding bone and annulus.

When the surgeon has completely enucleated or partially enucleated the disk space 121 to the extent desired, the blade positioning knob 14 is moved proximally or rotated in a direction which causes the drive stem 21 to move proximally (i.e., in the direction of arrow A in FIG. 2) again causing the proximal end 23b of the stem cap 23 to engage the retracting ledge 35 of the blades 26 thereby returning the blades 26 to the retracted position. The shape of the blade openings 27, the blades 26, the inner sheath 24, and the probe body 22 naturally deters foreign matter such as fragments of the nucleus pulposus, bone matter and the like from being trapped between the blades 26 and other parts of the diskectomy instrument 12. The diskectomy instrument 12 can then be moved proximally by pulling on the blade rotation knob 16 removing the distal end 12a of the diskectomy instrument 12 from the small gap and subsequently the entire diskectomy instrument 12 from the working tube 50 and/or from the body so that the enucleated disk matter can be removed under fluoroscopy or endoscopy by conventional devices such as forceps, graspers, suction devices, and the like.

While in the presently preferred embodiment there is shown a simple knob (the blade positioning knob 14) connected to the drive stem 21 which is used to radially extend and retract the blades 26, other actuation devices may be utilized without departing from the present invention. The actuator mechanism 13 or simply the actuator 13 is coupled to the proximal end 21b of the drive stem 21 to effectuate proximal and distal movement of the drive stem 21 linearly within the elongate body 18. In one alternate embodiment, the actuator 13 is the positioning knob 14 that is configured to rotate in a first direction to cause the drive stem 21 to move distally and to rotate in a second direction to cause the drive stem to move proximally. In an another alternate embodiment, the blade positioning knob 14 is separately coupled to the actuator 13. Preferably, the blade positioning knob 14 includes incremental indication marks 15 which at least generally correspond to the radial position of the blades 26 relative to the elongate body 18. The incremental indication marks 15 would also provide the surgeon with a gauging or measuring feature of the diskectomy tool 12 allowing the surgeon to measure the intervertebral space 121 prior to inserting any device. The surgeon simply rotates the positioning knob 14 until the blades 26 are firmly touching vertebrae 100 and then can read the distance using the incremental indication marks 15.

Figure 11:
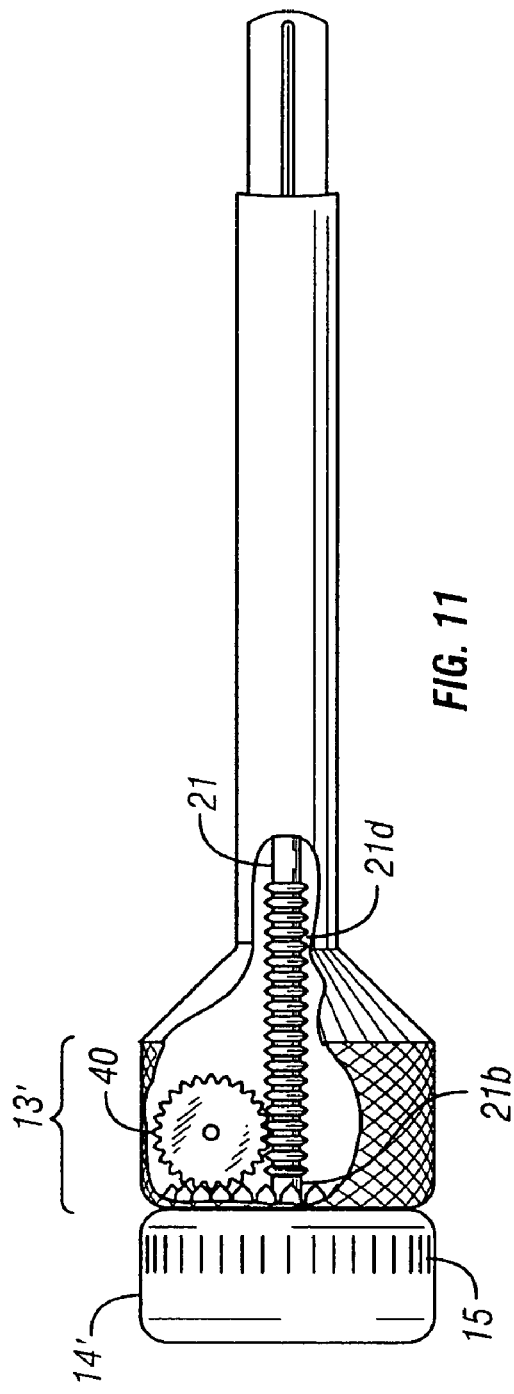
FIG. 11 is a side elevational view of a first actuator mechanism for a diskectomy instrument in accordance with the present invention.

FIG. 11 shows another embodiment of an actuator 13'. The proximal end 21b of the drive stem 21 is externally toothed (teeth 21d) and the actuator 13' includes a drive gear 40. The actuator 13' is rotatably mounted to the proximal end 18b of the elongate body 18 in such a manner that the teeth 21d of the drive stem 21 are in mesh engagement with the drive gear 40 of the actuator 13'. Rotation of the drive gear 40 in a first direction causes the drive stem 21 to move distally and rotation of the drive gear 40 in a second direction causes the drive stem 21 to move proximally. One possible rotatable blade positioning knob 14' is depicted as being disposed proximally to a blade rotation knob 16' and has teeth 14a' engaged with the drive gear 40.

Figure 12:
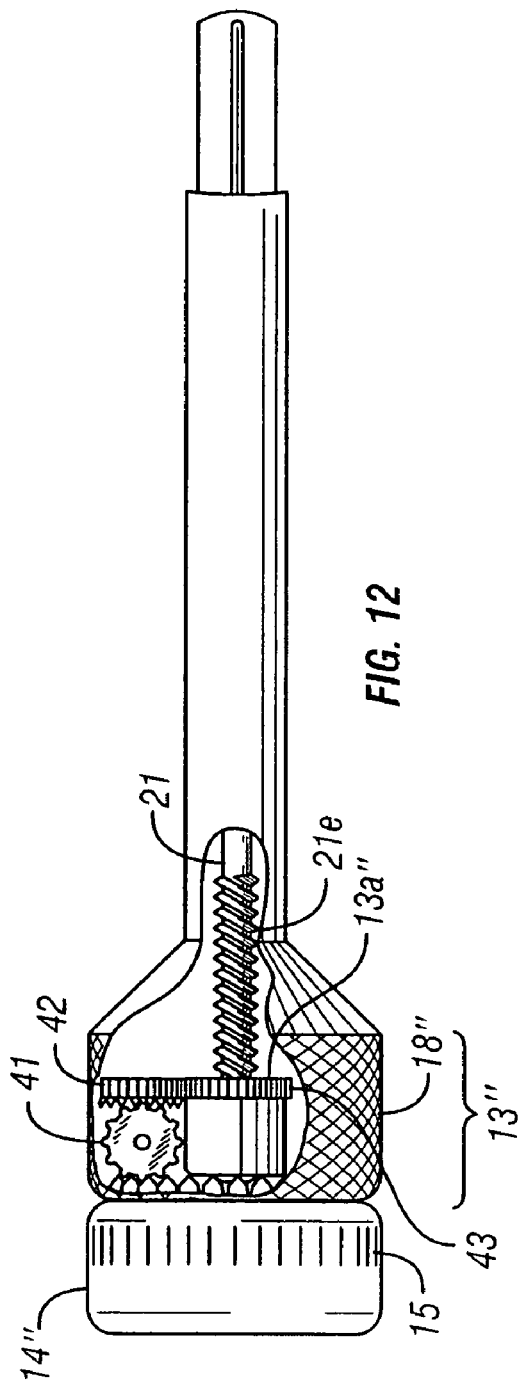
FIG. 12 is a side elevational view of a second actuator mechanism for a diskectomy instrument in accordance with the present invention.

FIG. 12 shows another embodiment of an actuator 13" where the proximal end 21b of the drive stem 21 is externally threaded (threads 21e) and the actuator 13" is internally threaded (threads 13a"). The actuator 13" is rotatably mounted to the proximal end 18b of the elongate body 18 in such a manner that the external threads 21e of the drive stem 21 are in threaded engagement with the internal threads 13a" of the actuator 13". Rotation of the actuator 13 in a first direction causes the drive stem 21 to move distally and rotation of the actuator 13 in a second direction causes the drive stem 21 to move proximally by translation of the internal and external threads 13a", 21e", respectively. The actuator 13" preferably includes a plurality of suitable reduction gears 42-43 as is known in the art to enable a user to precisely position the blades 26. One possible rotatable blade positioning knob 14" is depicted as being disposed proximally to a blade rotation knob 16" and has teeth 14a" engaged with the drive gear 41.

In another alternate embodiment (not shown), the drive stem 21 is actuated using scissors-like hand grips which may or may not have mechanical stops or limits for adjusting how far the drive stem is extended distally. It should be recognized that the particular method of actuating the drive stem 21 is not critical to the present invention.

Although the blade rotation knob 16 is depicted as having a knurled or textured surface, the blade rotation knob 16 may also be more complex without departing from the broad scope of the present invention. For example, in another alternate embodiment, the handle may be a two-piece assembly wherein a ratchet mechanism 17 is located between, for example, an inner and outer piece, allowing the surgeon to use partial turns of the blade rotation knob 16 effectuate rotation of the at least one blade in the cutting direction (i.e., to rotate the blades 26 in one direction).

In another alternate embodiment, a more complex mechanical assembly may include a side handle gearedly connected by directional translation gears, such as worm gears, helical gears, bevel gears and the like, to a rotational drive gear (not shown) connected to the probe assembly 20 allowing the surgeon to crank the side handle in a fashion similar to an egg beater thereby rotating the probe assembly 20 including the blades 26 in the cutting direction.

It should be obvious that the relative location of the blade rotation knob 16 and the blade positioning knob 14 is not critical to the present invention. For example, the blade positioning knob 14 may alternatively be disposed on the proximal portion of the elongate body 18 and the blade rotation knob 16 may be disposed proximal to the blade positioning knob 14.

Figure 13A:
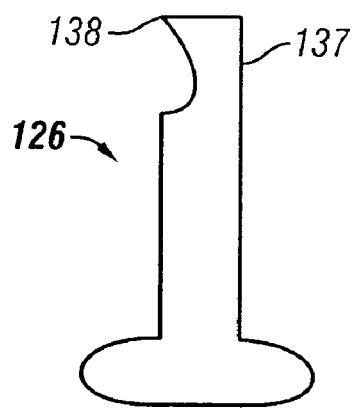
FIGS. 13A-13E are greatly enlarged sectional views of several preferred embodiments of diskectomy blades in accordance with the present invention.
Figure 13B:
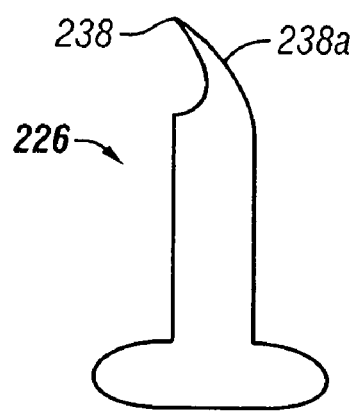
Figure 13C:
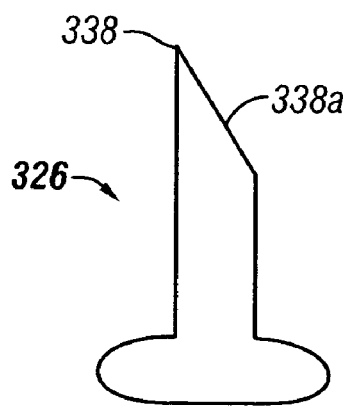
Figure 13D:
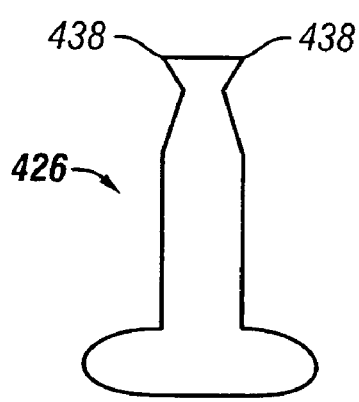
Figure 13E:
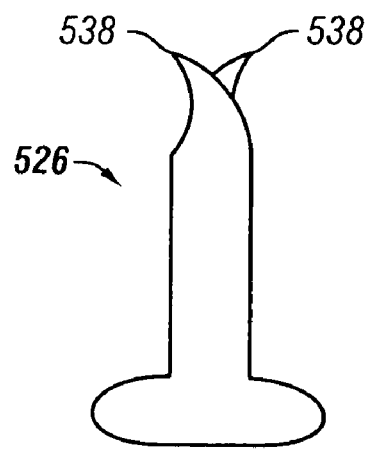

FIGS. 13A-13E are greatly enlarged sectional views of several preferred embodiments of diskectomy blades in accordance with the present invention. FIG. 13A shows a diskectomy blade 126 having a single sharpened edge 138 and a substantially box-like backing 137 for added structural support to the sharpened edge 138 of the diskectomy blade 126. The diskectomy blade 126 is a unidirectional type diskectomy blade which cuts in only one direction. FIG. 13B shows another diskectomy blade 226 having a single sharpened edge 238, however the back 238a of the sharpened edge 238 is generally rounded or sloped. The diskectomy blade 226 is also a unidirectional type diskectomy blade. FIG. 13C shows another diskectomy blade 326 having a single sharpened edge 338 and a generally sloped flat back 338a of the sharpened edge 138, 238, 338. The diskectomy blade 326 is also a unidirectional type diskectomy blade. Obviously, the sharpened edge 138, 238, 338 of all of the unidirectional type diskectomy blades 126, 226, 326 could face in the opposite direction of those shown without departing from the present invention. FIG. 13D shows a diskectomy blade 426 that has a pair of oppositely facing sharpened edges 438. The diskectomy blade 426 is a bidirectional type diskectomy blade which cuts when rotating in either direction (clockwise or counterclockwise rotation). FIG. 13E shows a serrated diskectomy blade 526 having multiple sharpened edges 538 alternately disposed along its length, and therefore, the diskectomy blade 526 is another bidirectional type diskectomy blade.

Figure 13F:
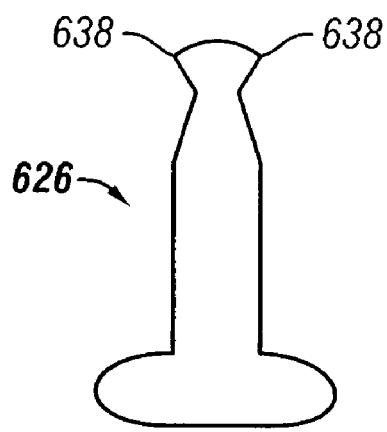
FIGS. 13F-13G are greatly enlarged sectional views of additional preferred embodiments of diskectomy blades in accordance with the present invention.
Figure 13G:
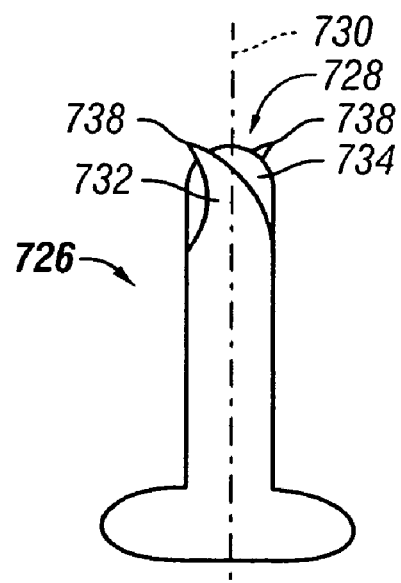
Figure 13H:
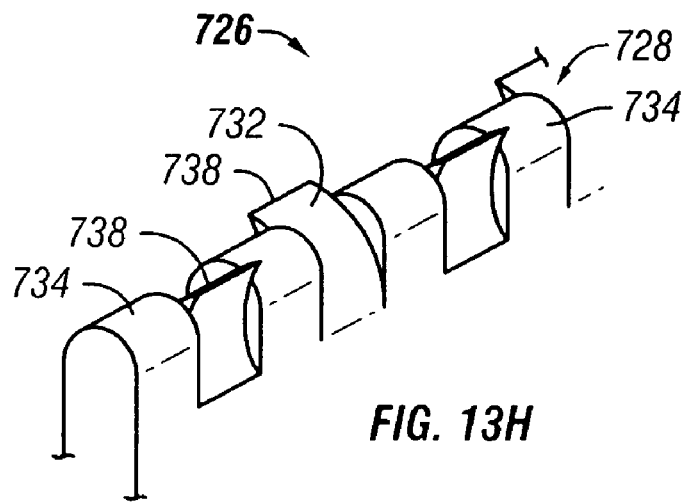
FIG. 13H is a perspective view of the diskectomy blade of FIG. 13G.
Figure 14:
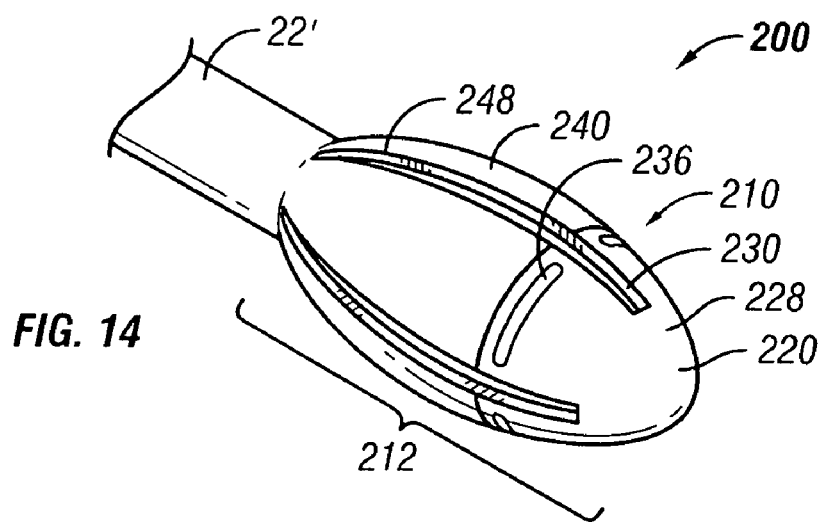
FIG. 14 is an enlarged side perspective view of a terminal end of a diskectomy instrument in accordance with a second preferred embodiment of the present invention, shown with diskectomy blades in a retracted position.
Figure 15:
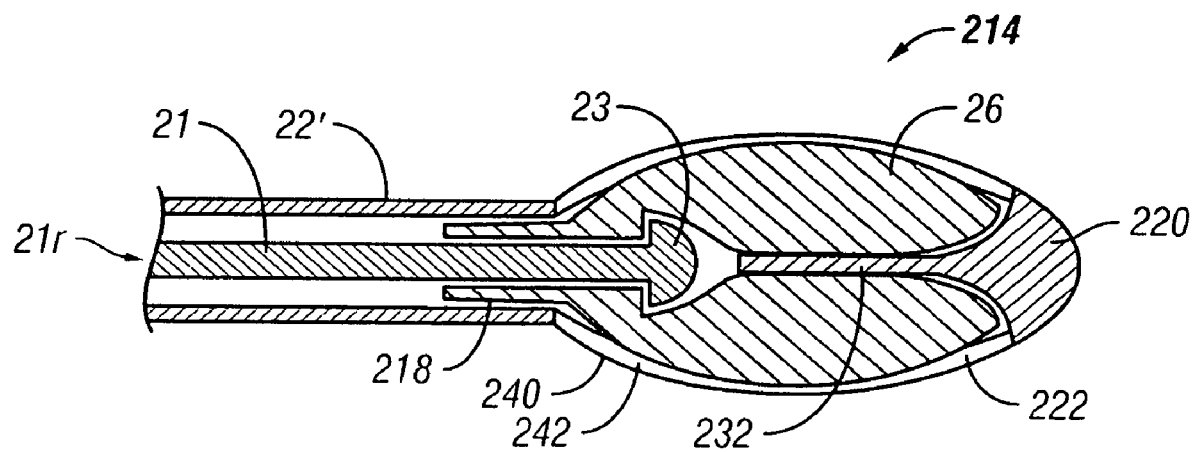
FIG. 15 is a cross section view of the diskectomy instrument of FIG. 14.
Figure 16:
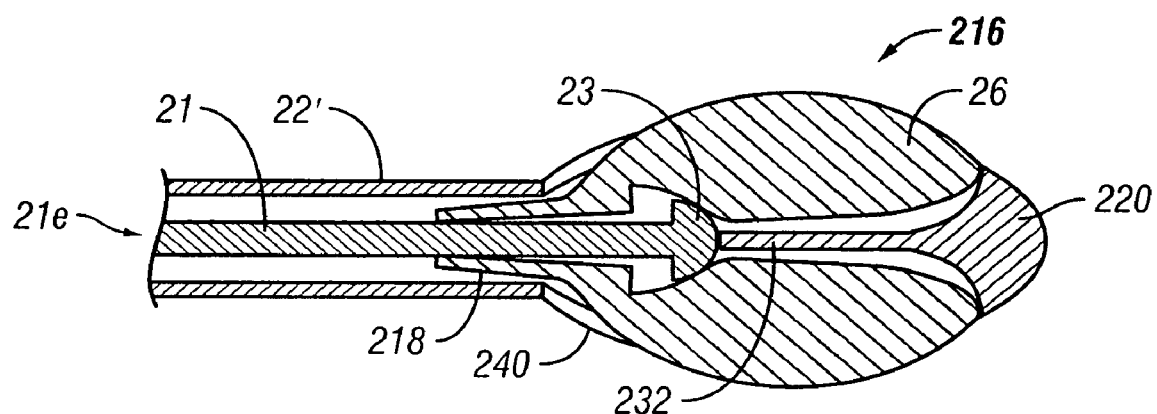
FIG. 16 is a cross-section view of the diskectomy instrument of FIG. 14, shown with the diskectomy blades in an extended position.

FIGS. 13F-13G are greatly enlarged sectional views of additional preferred embodiments of diskectomy blades in accordance with the present invention. FIG. 13F shows a diskectomy blade 626 that has a pair of oppositely facing sharpened edges 638. The diskectomy blade 626 is a bidirectional type diskectomy blade which cuts when rotating in either direction (clockwise or counterclockwise rotation). FIG. 13G shows a serrated diskectomy blade 726 having multiple sharpened edges 738 alternately disposed along its length with spacers 734 therebetween, and therefore, the diskectomy blade 726 is yet another bidirectional type diskectomy blade. FIG. 13H is a perspective view of the diskectomy blade of FIG. 13G which more clearly shows the alternating pattern of sharpened edges 738 facing in opposing directions with the spacers 734 therebetween.

In particular, with continued reference to FIGS. 13G and 13H, the bi-directional diskectomy blade 726 includes an edge 728 having a central plane 730 and a plurality of cutting elements 732 arranged along the edge 728, each cutting element 732 having a sharpened cutting edge 738. Adjacent cutting elements 732 are separated by blunt spacer elements 734. Preferably the cutting edges 738 of a first set of the plurality of cutting elements 732 are substantially parallel to the central plane 730 and are offset by a predetermined distance to a first side of the central plane 730 and cutting edges 738 of a second set of the plurality of cutting elements 732 are substantially parallel to the central plane 730 and are offset by a predetermined distance to a second side of the central plane 730. The cutting elements 732 of the first set are positioned along the edge 728 in an alternating pattern with cutting elements 732 of the second set.

Referring to FIGS. 14-17, a second preferred embodiment diskectomy instrument 200 includes a disposable head assembly 210. The disposable head assembly 210 comprises a first housing portion 220 which is releasably connectable to a second housing portion 240 to form a blade housing assembly 212. The disposable head assembly 210 further comprises at least one, and preferably a plurality of blades 26 (alternatively, any of the blades 126-726 could also be used with the second embodiment diskectomy tool 200). The blades 26 are movable between a retracted position 214 and an extended position 216 under action of the axially movable blade drive stem 21. A blade tail 218 is provided at the blade tail end 26b (see FIGS. 4 and 5). The blade tail 218 operates to retain the blade 26 to which it is connected within the blade housing assembly 212. As discussed above, the shape of the blades 26 deters foreign matter from being trapped between the blades 26 and a remainder of the diskectomy instrument 200.

Other than the blade housing assembly 212, the second embodiment diskectomy instrument 200 is generally similar to the first embodiment diskectomy instrument 12. In particular, the second embodiment diskectomy instrument 200 includes blades 26, actuator 13 (or actuators 13' or 13"), and drive stem 21, elements common with first embodiment diskectomy instrument 12. The drive stem 21 includes stem cap 23 fixedly connected to the first (distal) end 21a of the drive stem 21, while the drive stem 21 is releasably connectable at the second (proximal) end 21b to actuator 13. As with the first embodiment diskectomy instrument 12, the actuator 13 (or 13' or 13") is capable of controlling linear movement of the drive stem 21 between a first, retracted, position 21r and a second, extended, position 21e. The releasable connection between the drive stem 21 and the actuator 13, 13', 13" is preferably conventional.

The second embodiment diskectomy instrument 200 further includes a second embodiment probe body 22', generally similar to the probe body 22. The second embodiment probe body 22' includes second housing portion 240, which is fixedly attached, and is preferably integrally and unitarily formed with the second embodiment probe body 22'. Preferably, the second embodiment probe body 22' is fabricated from a rust-resistant, surgical-grade metal, such as 316 stainless steel or titanium.

Figure 17:
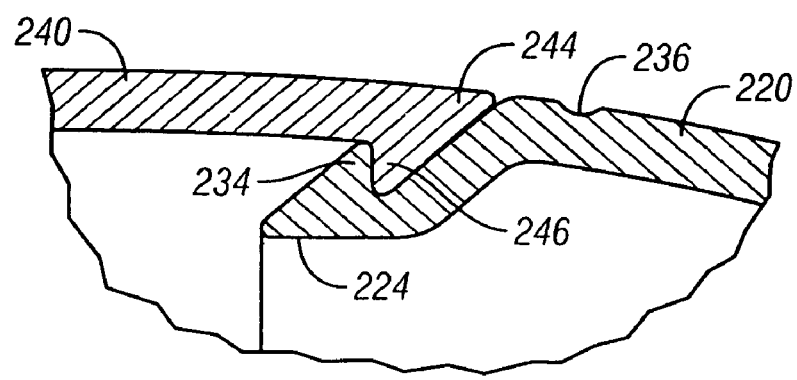
FIG. 17 is a greatly enlarged detail view of a releasable joint between first and second housing portions of a blade housing assembly of the diskectomy instrument of FIG. 14.
Figure 18:
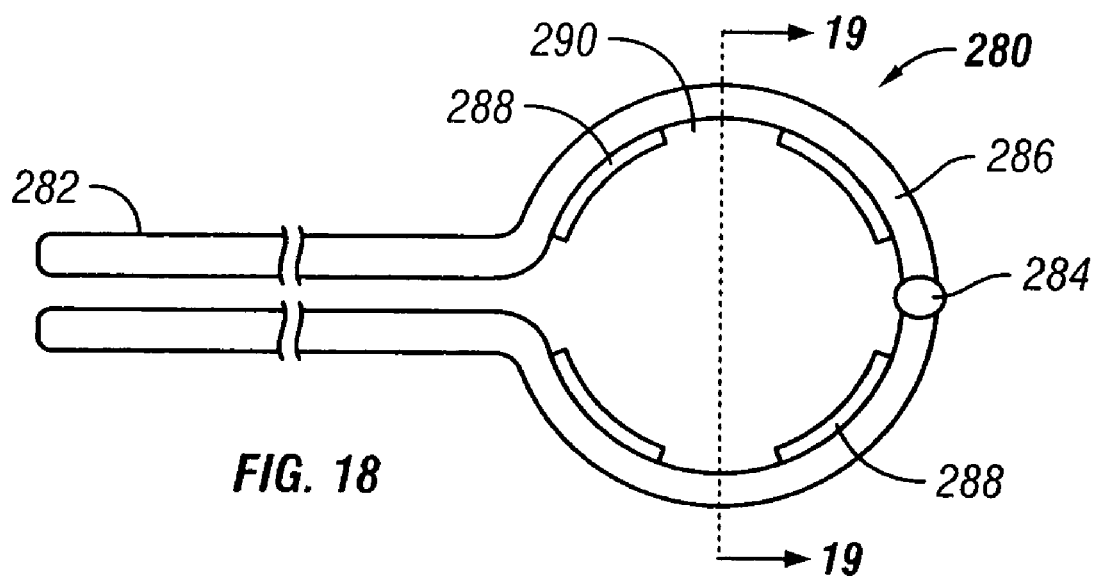
FIG. 18 is a side elevation view of a tool to facilitate removal of the first housing portion from the second housing portion of the diskectomy instrument of FIG. 14.

With continued reference to FIGS. 14-17, as well as to FIG. 18, the first housing portion 220 has an outer wall 222 shaped generally as a bullet nose. The first housing portion outer wall 222 has a trailing edge 224 and a nose 228. At least one, and preferably a plurality (for example, four) of blade openings 230 are formed in the outer wall 222, preferably spaced circumferentially at equal angles. The blade openings 230 are sized to receive the corresponding plurality of blades 26 with minimal lateral clearance. Preferably each blade opening 230 has a lateral spacing closely toleranced relative to a lateral thickness of the blades 26, for example, the blade opening lateral spacing may be no more than 0.050 inches greater than a lateral thickness of the blade 26 proximate edges of the blade opening 230 when the blade 26 is in the extended position. With minimal lateral clearance, the blades 26 are laterally supported by the blade openings 230 with only minimal lateral deflection of the blades 26. Furthermore, during use the minimal lateral clearance helps prevent foreign material from being trapped between a blade 26 and an edge of the blade opening 230, the foreign material thus hampering retraction of the blades 26. A blade stop 232 may be provided if needed to limit movement of the blades 26 in the recessed position 214, and to maintain position of the blades 26 within the blade openings 230. The blade stop 232, if provided, extends centrally within the interior of the first housing portion 220. With the blades 26 in the retracted position 214, the blades 26 are held in position within the housing assembly 212, with the blade sharpened edges 38 captured within the blade openings 230 and the inner faces 30 resting against the blade stop 232. Removal tool alignment recesses 236 are provided between the blade openings 230 to facilitate use of a removal tool 280 described below.

The second housing portion 240 has an outer wall 242 sized and shaped to mate with the first housing portion outer wall 222, forming a generally smooth convex exterior profile for the blade housing assembly 212. The second housing portion outer wall 242 has a forward edge 244. The forward edge 244 is adapted to mate with the first housing portion outer wall trailing edge 224. Likewise, the second housing portion 240 is provided with a plurality of blade openings 248 sized, shaped, and positioned to mate with the first housing portion blade openings 230. Thus, blade openings are preferably formed as a combination of the first housing portion blade openings 230 and the second housing portion blade openings 240. Alternatively, the blade openings could be formed entirely in either the first or second housing portions 220, 240.

With particular reference to FIG. 17, the first and second housing portions 220, 240 are preferably releaseably connected by inter-engaging latching members. In the embodiment illustrated, the latching members are circumferentially-extending lips. In particular, the first housing portion 220 has a circumferential lip 234 provided with a hook portion. Similarly, the second housing portion 240 has a mating circumferential lip 246 which releasably engages the first housing portion circumferential lip 234. The circumferential lips 234, 246 are broken by the blade openings 230, 248, thus forming a gap in the circumferential lips 234, 246 at each blade opening 230, 248. With the first and second housing portions assembled, the blades 26 are captured within the housing assembly 212. Other types of inter-engaging latching members could be used, for example one or more flexible tongues extending from one of the housing portions 220 or 240. For example, each tongue could be provided with a protrusion which is received in a mating recess formed in the wall of the other of the housing portions 220, 240.

Preferably, the first housing portion 220 is fabricated from a readily molded, transparent polymeric material having good strength characteristics, such as the material sold under the trademark LEXAN®.

In one preferred method of assembly, the disposable head assembly 210 is assembled by inverting first housing portion 220 (with nose 228 pointed downward), and then installing the blades 26 in the first housing portion 220. Interaction of each blade inner face 30 with edges of blade openings 230 prevents the blades 26 from falling out of first housing portion 220. The blades 26 and first housing portion 220 are preferably packaged and shipped to the end user as an assembly.

The first housing portion 220 and blades 26 are assembled to a remainder of the second embodiment diskectomy instrument 200 preferably by first installing the stem cap 23 within the notches 34 of the blades 26. The assembly of the drive stem 21, blades 26, and first housing portion 220 is then assembled with the remainder of the diskectomy instrument 200, with the drive stem second or proximal end 21b being releasably engaged with the actuator 13, and the first housing portion 220 being releasably engaged with the second housing portion 240. Once assembled, the blade edges 38 are held within and laterally supported by edges of blade openings 230, 248 in both the retracted and extended positions 214, 216. The blades 26 thus prevent significant rotation of the first housing portion 220. As the second housing portion blade openings 248 are rigidly fixed in position, and the first housing portion 220 is capable of slight rotational movement relative to the second housing portion 240, the torque necessary to rotate the blades 26 during use on a patient is transferred to the blades 26 by the second housing portion 240. Thus, the first housing portion 220, preferably fabricated from less robust materials than the second housing portion 240, is subjected to minimal loading during use.

In use, the second embodiment diskectomy instrument 200 operates similarly to the first embodiment diskectomy instrument 12 as discussed above. Additionally, it may be desirable with both the first and second embodiment diskectomy tools 12, 200 to provide an external marking on the probe body 22, 22' to assist the surgeon in gauging the depth to which the instrument 12, 200 has been inserted into a patient. The marking could be, for example, an indelible color marking on the probe body 22, 22', or a protruding ring affixed to the probe body 22, 22'.

Figure 19:
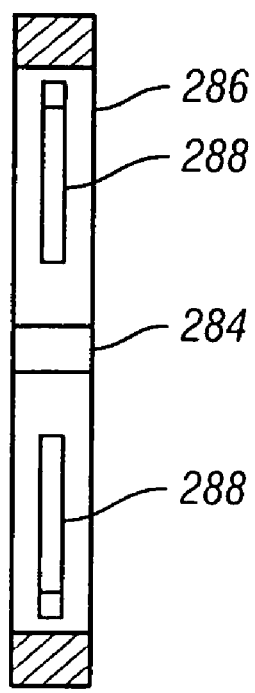
FIG. 19 is a cross-section view of the tool of FIG. 18, taken along line 19-19 of FIG. 18.

With reference now to FIGS. 18 and 19, after use, the removal tool 280 is used to flex one of the first and second housing portions out of engagement with the other housing portions by applying force to an exterior surface of the blade housing assembly 212. In the embodiment illustrated, the removal tool 280 is used to flex the trailing edge 224 of the first housing portion 220, moving the first housing lip 234 out of engagement with the second housing portion lip 246, allowing the first housing portion 220, the blades 26, and the drive stem 21 to be separated from a remainder of the second embodiment diskectomy tool 200.

The removal tool 280 includes first and second handles 282 connected by a hinge 284. An interior portion of each handle 282 proximate the hinge 284 is provided with a clamp section 286, each clamp section 286 having alignment protruding elements 288. The protruding elements 288 are positioned, sized, and shaped to engage the alignment recesses 236. Gaps 290 are provided between adjacent protruding elements 288. The gaps 290 prevent the protruding elements 288 from contacting the blades 26 during the process of removing the first housing portion 220 from the second housing portion 240.

The user begins the disposable head assembly 210 removal process by moving the blades 26 to the retracted position 214. The removal tool 280 is placed around the blade housing assembly 212, in a position such that as the handles 282 are closed around the housing assembly 212, with the alignment protruding elements 288 engaging the alignment recesses 236. As the handles 282 are fully closed, the protruding elements 288 engage and press on an exterior surface of the blade housing assembly 212 (as illustrated, the first housing portion outer wall 222), flexing the first housing portion lip 234 out of engagement with the second housing portion lip 246, allowing the user to pull the first housing portion 220 out of engagement with the second housing portion 240 and the drive stem 21 out of engagement with the actuator 13. Once separated from the remainder of the diskectomy tool 200, the disposable head 210 (including the first housing portion 220 and the blades 26) is preferably discarded.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A diskectomy instrument comprising:
   an elongate body;
   a blade housing extending from a distal end of the elongate body and having a convexly-shaped exterior profile, a completely closed, bluntly tapered, smooth distal end and at least one blade opening proximate the distal end and extending toward the elongate body, an outermost diameter of the blade housing being larger than an outermost diameter of the elongate body;
   at least one blade movably mounted at least partially within the blade housing proximate the at least one blade opening, the at least one blade having a distal end, a proximal end, at least one sharp convexly shaped cutting edge extending at least partially between the distal end and the proximal end of the blade housing, at least one projection extending generally perpendicularly from a sidewall of the at least one blade and a stem mating portion;
   a drive stem movably mounted within the elongate body and having a distal end, a proximal end being toothed or threaded and a blade mating portion;
   an actuator having a drive gear located therein, the drive gear being operatively connected to at least a portion of the proximal end of the drive stem;
   wherein the drive stem slidably engages the at least one blade when the drive stem is moved distally by movement of the drive gear, thereby moving the distal and proximal ends of the at least one blade radially away from and generally parallel to a longitudinal axis of the diskectomy instrument and outwardly through the at least one blade opening and not at or beyond a distal end of the diskectomy instrument, the blade mating portion being configured to cooperatively engage the stem mating portion of the at least one blade when the drive stem is moved proximally by movement of the drive gear thereby retracting the at least one blade into the blade housing, and wherein interaction of the at least one projection of the at least one blade with a side of the at least one blade opening prevents an edge opposite the cutting edge of the at least one blade from coming out of the blade housing.

2. The diskectomy instrument of claim 1, the blade housing including at least one removal tool alignment recess formed in an exterior surface of the blade housing.

3. The diskectomy instrument of claim 1, wherein the drive stem is releasably connectable to the actuator.

4. The diskectomy instrument of claim 1, wherein the at least one blade opening has a lateral spacing closely toleranced relative to a lateral thickness of the at least one blade proximate edges of the at least one blade opening.

5. The diskectomy instrument of claim 1, wherein the at least one blade is a bi-directional blade comprising an edge having a central plane and a plurality of cutting elements arranged along the edge, each cutting element having a sharpened cutting edge, wherein adjacent cutting elements are fixed with respect to each other and are separated by blunt spacer elements, each blunt spacer element having an arcuate tip and a width generally equal to a width of each cutting element.

6. The diskectomy instrument of claim 1, wherein the at least one blade further comprises a notch including a ramped portion and a retracting ledge configured to engage with the blade mating portion of the drive stem of the diskectomy instrument to extend and retract the at least one blade.

7. The diskectomy instrument of claim 1, wherein the blade housing has a releasably mounted distal portion.

8. The diskectomy instrument of claim 1, further comprising:
   at least three blade openings circumferentially spaced at equal angles in the blade housing; and
   at least three blades movably mounted at least partially within the blade housing, each blade being proximate one of the at least three blade openings.

* * * * *